| United States Patent [19] | [11] Patent Number: 4,789,670 |
| Tipton et al. | [45] Date of Patent: Dec. 6, 1988 |

[54] METHOD AND COMPOSITIONS FOR SUPPRESSION OF ATHEROGENESIS UTILIZING CHOLESTEROL HYDROPEROXIDES

[75] Inventors: Carl L. Tipton; Donald C. Beitz, both of Ames, Iowa

[73] Assignee: Iowa State University Research Foundation, Inc., Ames, Iowa

[21] Appl. No.: 15,947

[22] Filed: Feb. 18, 1987

[51] Int. Cl.$^4$ ............................................. A61K 31/56
[52] U.S. Cl. ..................................... 514/182; 514/824
[58] Field of Search ......................................... 514/182

[56] References Cited

PUBLICATIONS

J. Org. Chem., vol. 38, No. 1 (1973), pp. 119–123; Teng et al.
J. Org. Chem., vol. 35, No. 8 (1970), pp. 2627–2632; VanLier et al.
Chemical Abstracts, vol. 106 (1987), #3176k; Highley et al.

*Primary Examiner*—Leonard Schenkman
*Assistant Examiner*—Joseph A. Lipovsky
*Attorney, Agent, or Firm*—Tilton, Fallon, Lungmus & Chestnut

[57] ABSTRACT

Atherogenesis is suppressed by administering cholesterol hydroperoxide in an amount effective for reducing aortal deposit of cholesterol. The cholesterol hydroperoxide may be administered in an oral dose form.

14 Claims, No Drawings

METHOD AND COMPOSITIONS FOR SUPPRESSION OF ATHEROGENESIS UTILIZING CHOLESTEROL HYDROPEROXIDES

FIELD OF INVENTION

The field of the invention is medicinal agents and methods for combatting atherogenesis.

BACKGROUND OF INVENTION

The role of cholesterol oxidation products in atherogenesis has long been a controversial topic. Peng and Taylor (1983), for example, argue that cholesterol oxidation products may be responsible for an initial arterial cell injury that eventually results in atherosclerosis. On the other hand, Higley et al. (1986) claim that oxidized cholesterol is substantially less atherogenic than purified cholesterol. Peng and Taylor, in Perkins and Visek, eds., "Dietary Fats and Health" (American Oil Chemists Society, Champaign, Ill., 1983), pp. 919–933; and Higley et al. (1986), Atherosclerosis, 62:91–104.

Hypercholesteroloemia is widely considered to be a major risk factor for the development of atherosclerosis. The lowering of blood cholesterol levels has therefore been an important goal in the search for ways to prevent or treat atherosclerosis. Medicinal agents reported as reducing development of atherslerotic lesions typically result in the lowering of blood cholesterol levels. Beneficial agents which do not affect blood cholesterol are rare. But Bell and Schaub (1986) have reported that chlorpromazine reduced the development of such lesions in rabbits fed an atherogenic diet without lowering of blood cholesterol. Chlorpromazine may function as an inhibitor of calmodulin (Gietzen, 1986), but it is classified pharmacologically as a tranquilizer and sedative (Merck Index, 1976, page 280), and therefore is not likely to be useful as a treatment for atherosclerosis. Bell and Schaub (1986), Arteriosclerosis, 6:42–48; and Gietzen (1986), in Baker, et al., eds. "Intracellular Celcium Regulation" (Manchester University Press, Manchester, U.K.), pp. 405–423.

SUMMARY OF INVENTION

A mixture of cholesterol autoxidation products, prepared from an aged sample of cholesterol by recrystallization of the cholesterol from methanol, inhibits calmodulin irreversibly in a $Ca^{2+}$-dependent reaction. The mixture was effective at less than 1 $\mu$M. The reactive material is destroyed by reduction with $NaBH_4$, $NaCNBH_3$, or NaI, from which we concluded that the calmodulin inhibition is due to the cholesterol hydroperoxides.

These hydroperoxides were purified further by partition between ethyl ether and 0.1 N NaOH followed by chromatography on Sephadex LH-20. The partially purified hydroperoxides were used in feeding experiments with young adult white rabbits. The animals were fed Purina Rabbit Chow to which was added 1% cholesterol, or cholesterol hydroperoxides (50 mg/day), or both, or nothing. After 8 weeks, the animals were killed, and the aortas were stained with Sudan IV. Cholesterol caused extensive atheroma formation, but the addition of cholesterol hydroperoxides markedly reduced atheroma formation. In a second experiment, these results were repeated with the additional observation that the chemically reduced material (without hydroperoxides) was ineffective in suppressing atheroma formation. It was also observed that cholesterol hydroperoxides do not lower cholesterol concentrations in blood plasma, liver or heart.

The foregoing results led to this invention, which in one of its aspects is a method of suppressing cholesterol-induced atherogenesis in human patients by administering to the patient an amount of a cholesterol hydroperoxide effective for reducing aortal deposit of cholesterol. It is believed that cholesterol hydroperoxides as a class, since they all contain a similar hydroperoxide group, can be employed. Certain cholesterol hydroperoxides are relatively more abundant in air-oxidized cholesterol, and/or can be more readily prepared by a more specific synthesis. These more available hydroperoxides are therefore preferred; namely, (1) 3$\beta$-hydroxycholest-5-ene-7$\alpha$-hydroperoxide, (2) 3$\beta$-hydroxycholest-5-ene-7$\beta$-hydroperoxide, and (3) 3$\beta$-hydroxycholest-5-ene-25-hydroperoxide, as well as mixtures thereof.

The present invention also includes medications for prevention and/or treatment of cholesterol-induced atherogenesis in human patients, which comprise oral dose forms of one or more cholesterol hydroperoxides. Tablets or capsules can be used, but the medicinal composition of this invention are not limited thereto. Cholesterol hydroperoxide may be admixed with solid carriers. In tablet form, the cholesterol hydroperoxide may be admixed with a pharmaceutical tableting composition and formed into tablets. For use in the form of a capsule, the cholesterol hydroperoxide may be admixed with a pharmaceutical diluent composition, and filled into orally administerable capsules.

DETAILED DESCRIPTION

Cholesterol oxidizes readily in contact with air, and the oxidation proceeds at ambient room temperature. The oxidation products as initially formed are largely cholesterol hydroperoxides. See Smith, "Cholesterol Auto-oxidation" (1981, Plenum Press, New York). This reference lists the initial auto-oxidation products in Table 11, pages 238 to 239. These include 3$\beta$-hydroxycholest-5-ene-7$\alpha$-hydroperoxide; 3$\beta$-hydroxycholest-5-ene-7$\beta$-hydroperoxide; and 3$\beta$-hydroxcholest-5-ene-25-hydroperoxide, which are presently preferred for use in this invention. Other hydroperoxides formed include 3$\beta$-hydroxycholest-5-ene-17-hydroperoxides; 3$\beta$-hydroxycholest-5-ene-20-hydroperoxides; 3$\beta$-hydroxycholest-5-ene-22-hydroperoxides; and 3$\beta$-hydroxycholest-5-ene -24-hydroperoxides. Each of these compounds contain a hydroperoxide group with chemically similar properties.

When it is desired to accelerate the oxidation of cholesterol to hydroperoxides, a photochemical oxidation procedure can be employed as described by Schenk et al. (1958) "Liebigs Ann. Chem.", 618:202–211. This reference describes the preparation and isolation of 3$\beta$-hydroxycholest-5-ene-7$\alpha$-hydroperoxide. The 7-$\beta$ isomer of this compound can be synthesized and isolated as described by Teng et al. (1973), J. Org. Chem. 38:119–123. Other of the cholesterol hydroperoxides can be prepared as an oxidized mixture, and separated by fractionation. See van Lier et al. (1970), J. Org. Chem., 35:2627–2632. The cholesterol hydroperoxides are preferably administered orally but other methods of administration can be employed, such as incorporation into liposomes or into slow release pellets.

The amount of cholesterol hydroperoxide to be administered can be related to the body weight and/or the blood cholesterol level of the patient. A sufficient amount of the cholesterol hydroperoxide should be administered to be effective for reducing aortal deposit of cholesterol. For example, from 0.5 to 25 milligrams (mg) of cholesterol hydroperoxide can be orally administered per kilogram (kg) of body weight per 24 hours. The administration should be on a regular basis for a period of time as required to prevent or treat cholesterol-induced atherogenesis. The cholesterol hydroperoxide may be prepared in the form of tablets or capsules. The hydroperoxide compounds, which are waxy solids, can be combined with tabletting compositions, viz. dextrose or sucrose, and formed into tablets. Conveniently, the tablets may contain an amount of the cholesterol hydroperoxide, so that 2 to 4 tablets per 24 hours may be taken. For example, each tablet may contain 12.5 mg for a two tablet dose, or 6.25 mg of cholesterol hydroperoxide for a four tablet dose per 24 hours.

The cholesterol hydroperoxides may also be prepared in capsule dose form. The capsules can contain only the cholesterol hydroperoxide, or it may be admixed with a pharmaceutical extender of diluent, such as lactose, dextrose, etc.

For oral administration, either in the form of tablets or capsules, the hydroperoxides may be administered in doses of from about 0.5 to 25 mg of cholesterol hydroperoxide per patient per 24 hours. If the cholesterol hydroperoxide composition includes oxidized derivatives of cholesterol other than the hydroperoxides, dosage should be on the basis of the hydroperoxide content only. The non-hydroperoxide derivatives of cholesterol are not effective for purposes of this invention.

The administration of cholesterol hydroperoxide could be monitored if desired. For example, a blood sample could be obtained and the serum separated with the lipoproteins therein. A portion of the serum could then be subjected to a cAMP-phosphodiesterase assay to measure calmodulin inhibition. Sharma and Wang (1979) *Adv. Cyclic Nucleotide Res.*, 10:187-198.

The experimental basis of the present invention is further illustrated by the following examples.

EXAMPLE I

Materials and Methods

The starting material for isolation of cholesterol hydroperoxides was a large sample of USP cholesterol which had been subjected to air oxidation by storage at room temperature for approximately 20 years. The isolation procedure was adapted from those of van Lier and Smith (1970) and Teng et al. (1973), both cited above. The yields given in the following procedure are averages from 14 preparations. Lots of 50 g of the aged cholesterol were dissolved in 1.5 l of hot methanol and cooled, yielding 37 g crystalline cholesterol. The filtrate was reduced to about 500 ml on a rotary evaporator and a second crop of crystals (5.0 g) was collected. The filtrate was then taken to dryness in vacuo, redissolved in ethyl ether, extracted with 0.1 N NaOH, washed with water and dried over anhydrous sodium sulfate. After removal of the ether the residue was dissolved in methylene chloride-acetone 9:1 (v/v) and chromatographed on a column of Sephadex LH-20. Fractions were examined by thin layer chromatography on silica gel, developed with benzene-methanol 8:1 (v/v); hydroperoxides were detected by spraying with N, N-dimethyl-p-phenylenediamine as described by Smith and Hill (1972) *J. Chromatog.*, 66:101–109. Cholesterol and cholesterol hydroperoxides overlapped on these columns; fractions eluting after the last detectable cholesterol were combined, yielding 2.03 g. Thin-layer chromatography shows that this material, which was used for the first feeding experiment, contained several compounds with the properties expected of cholesterol hydroperoxides.

For the second feeding experiment, a portion of the hydroperoxide-enriched material was treated with NaI to reduce the hydroperoxides. To a solution of the hydroperoxides in methanol was added a 1.5-fold molar excess of NaI (calculated on the assumption that the hydroperoxide-enriched material was entirely cholesterol hydroperoxides). After 3 hr, an excess of $Na_2S_2O_3$ was added; when the yellow color was nearly gone, the methanol solution was diluted with ethyl ether and water was added until two phases formed. The ether phase was separated, washed with water, dried and evaporated to dryness.

Feeding Experiments

For the first feeding experiment, eighteen young adult New Zealand white rabbits (2.7+/−0.3 kg) were divided into 5 groups. The first group (3 animals) was killed immediately and tissue samples obtained for comparison with the experimental animals. The controls (3 rabbits) were fed 160 g/day Purina Pelleted Rabbit Chow (Ralston Purina Co., St. Louis, MO.); the other three groups (4 rabbits each) received the same diet to which was added 1.6 g recrystallized cholesterol, or 50 mg of the cholesterol hydroperoxide-enriched material, or both 1.6 g recrystallized cholesterol and 50 mg of cholesterol hydroperoxides. The sterols were added to the pelleted diet in ethyl ether and the ether was allowed to evaporate under a stream of nitrogen. The animals were fed this diet for 61 days, during which time one animal on the cholesterol diet died of unknown causes. The weight gained by the animals during the experiment, as percent of initial weight, was: controls, 38%; cholesterol, 33%; hydroperoxides, 34%; and cholesterol plus hydroperoxides, 18%. At the end of the feeding period the animals were killed and blood and tissue samples obtained for further investigation.

A second feeding experiment was conducted in the same way as the first with the following changes. Twenty-six rabbits (2.8 +/−0.05 kg) were obtained; two were killed before the feeding experiment began and tissue samples obtained as before. The remaining animals were divided into 6 groups of 4. Four groups received the same diets as in the first experiment. The other two groups received 160/g day Purina Pelleted Rabbit Chow to which was added 50 mg/day of the material produced by reduction of the hydroperoxide-enriched material with NaI; or 1.6 g/day recrystallized cholesterol plus 50 mg/day of the reduced material. The animals received all six diets for 56 days, during which time one control animal and one receiving the hydroperoxide preparation died during removal of blood samples. The weight gain, as percent of initial weight, was: controls, 45%; cholesterol, 31%; hydroperoxides, 29%; cholesterol plus hydroperoxides, 31%; reduced hydroperoxides 35%, and cholesterol plus reduced hydroperoxides, 30%.

The aortas were sectioned longitudinally and stained with Sudan IV (Holman et al., 1958*Lat. Invest.*, 7:42–47). Serum lipoproteins were separated as described by Havel et al. (1955) *J. Clin. Invest.*, 34:1345–1353. Lipids were extracted by the method of Bligh and Dyer (1959) *Can. J. Biochem. and Physiol.*, 37:911–917 and free and esterified cholesterol concentrations in plasma, lipoproteins, and tissue were determined by the method of Sale (1984) *Anal. Biochem.*, 142:347-350.

Results

An examination of the aortas stained with Sudan IV revealed the following: As expected, the control aortas were completely free of atherosclerotic lesions while those from animals fed cholesterol were heavily infiltrated with fatty material. Feeding the material enriched in cholesterol hydroperoxides produced no lesions, and aortas from animals that received both cholesterol and hydroperoxides had substantially smaller areas covered by the lesions than those from animals receiving cholesterol alone. In the second experiment, the extent of the lesions in the animals fed cholesterol alone was less than in the first experiment, but the relationships among the treatments remains qualitatively the same. Aortas from animals fed material from which the hydroperoxides had been removed by treatment with NaI showed little or no lesion formation, while those from animals fed cholesterol plus the reduced material were essentially the same as those from animals fed only cholesterol. This result shows that the active agent in reducing cholesterol deposit was the cholesterol hydroperoxide.

Blood plasma cholesterol and cholesterol ester contents at the end of the feeding experiments are shown below in Table I (experiment 1) and Table II (experiment 2). The oxygenated cholesterol preparations had no significant effects on blood cholesterol and cholesterol ester levels.

Analyses of cholesterol and cholesterol esters in liver and heart samples from the first feeding experiment are shown in Table III. The hydroperoxides show no tendency to reduce the accumulation of sterol in these tissues when cholesterol is fed.

Discussion

The results reported here show that, in the rabbit, cholesterol hydroperoxides are able to decrease very substantially the extent of formation of atherosclerotic lesions in the aorta without lowering blood cholesterol levels and without decreasing uptake and storage of cholesterol by the liver and heart. The effect of the cholesterol hydroperoxides appears to be specific to vascular tissue.

TABLE I

Final values of blood plasma cholesterol and cholesterol esters, first feeding experiment.

| Treatment | Cholesterol mg/dL +/- S.D. | Cholesterol Esters mg/dL +/- S.D. |
|---|---|---|
| Control | 11 +/- 3 | 14 +/- 9 |
| + hydroperoxides | 10 +/- 2 | 14 +/- 5 |
| + cholesterol | 446 +/- 163 | 1507 +/- 361 |
| + cholesterol + hydroperoxides | 524 +/- 113 | 1424 +/- 554 |

TABLE II

Final values of blood plasma cholesterol and cholesterol esters, second feeding experiment.

| Treatment | Cholesterol mg/dL +/- S.D. | Cholesterol Esters mg/dL +/- S.D. |
|---|---|---|
| Control | 9 +/- 8 | 51 +/- 33+++ |
| + hydroperoxides | 7 +/- 3 | 36 +/- 3 |
| + NaI—hydroperoxides | 5 +/- 2 | 45 +/- 12 |
| + cholesterol | 828 +/- 459 | 1520 +/- 820 |
| + cholesterol + hydroperoxides | 820 +/- 58 | 2411 +/- 425 |
| + cholesterol + NaI—hydroperoxides | 484 +/- 104 | 1366 +/- 797 |

TABLE III

Cholesterol and cholesterol esters in liver and heart samples from the first feeding experiment.

| Treatments | cholesterol mg/100 g wet tissue +/- S.D. | cholesterol and esters mg/100 g wet tissue +/- S.D. |
|---|---|---|
| LIVER | | |
| Zero time control | 199 +/- 36 | 28 +/- 20 |
| Control diet | 229 +/- 23 | 35 +/- 18 |
| + hydroperoxides | 234 +/- 22 | 23 +/- 14 |
| + cholesterol | 1217 +/- 615 | 4960 +/- 1416 |
| + cholesterol + hydroperoxides | 1539 +/- 93 | 6136 +/- 890 |
| HEART | | |
| Zero time control | 75 +/- 19 | 18 +/- 9 |
| Control diet | 107 +/- 30 | 35 +/- 11 |
| + hydroperoxides | 41 +/- 11 | 5 +/- 4 |
| + cholesterol | 160 +/- 24 | 158 +/- 74 |
| + cholesterol + hydroperoxides | 201 +/- 26 | 275 +/- 114 |

EXAMPLE II

Materials and Methods

The air-oxidized cholesterol of Example I was recrystallized from methanol. The supernatant solution is referred to here as autoxidized cholesterol (AC). It is slightly yellow, and the dry residue, after evaporation of the methanol, is 26.8 mg/ml.

Testosterone, 4-cholesten-3-one, 5-cholesten-3$\beta$-ol-7-one (7-ketocholesterol), cholesterol-5$\alpha$,6$\alpha$-epoxide, and 5'-nucleotidase (*Crotalus atrox* venom) were obtained from Sigma Chemical Co., St. Louis, MO. All other chemicals used were of reagent grade.

Bovine brain calmodulin was purified to homogeneity according to the method described by Sharma and Wang (1979), cited above, with the inclusion of phenyl-Sepharose affinity chromatography as described by Dedman and Kaetzel (1983) *Methods Enzymol.*, 102:1-8. Calmodulin-deficient, calmodulin-dependent cyclic nucleotide phosphodiesterase from bovine brain was partially purified by the method described by Sharma et al. (1983) *Methods Enzymol.*, 102:210-219, with the omission of the calmodulin-Sepharose affinity chromatography. Calmodulin was assayed by the activation of the bovine brain calmodulin-dependent cyclic, nucleotide phosphodiesterase as described by Leung et al. (1982) *J. Biol. Chem.*, 259:2742-2747. Briefly, the phosphodiesterase reaction was coupled to the 5,'-nucleotidase reaction. The amount of phosphate released was measured by the malachite green method of Carter and Karl (1982) *J. Biochem. Biophys. Methods*, 7:7-13. One unit of calmodulin is defined as that amount giving 50% of the maximal activation of the phosphodiesterase.

Results and Discussion

Crystalline cholesterol autoxidizes slowly upon storage in contact with air, and a mixture of autoxidation products is obtained readily by recrystallization of old sample of cholesterol from Smith (1981), pp. 385–389, cited above. A sample obtained in this way inhibits the calmodulin-dependent phosphodiesterase at a 1:10 dilution but not at a 1:100 dilution (Table IV). Assuming an average molecular weight of 400, the final concentration of the mixture in the assays ranged from 37 µM to 0.37 µM. Considering the complexity of the mixture, any single autoxidation product would have been present at much lower concentration. The inhibition is due to reaction with calmodulin, rather than reaction with other components of the assay mixture, and the reaction is irreversible. This was shown by the experiment in which calmodulin was first incubated with the autoxidized cholesterol, then diluted for assay. This dilution reduced the concentration of auto-oxidized cholesterol below the level that was inhibitory in the whole assay mixture. The reaction is also $Ca^{2+}$-dependent, suggesting that only the active conformation of calmodulin reacts, and it is time-dependent. In these ways, the reaction of auto-oxidized cholesterol with calmodulin resembles the reaction of ophiobolin A (Leung et al., 1984, cited above).

Reduction of the auto-oxidized cholesterol solution with sodium borohydride greatly reduced the absorbance at 335 nm, whereas sodium cyanoborohydride had little effect. But both these treatments destroyed the inhibitory property of the auto-oxidized cholesterol. Thus, the inhibitor probably was not an $\alpha,\beta$-unsaturated ketone. Treatment with sodium iodide also destroyed the inhibitor. This treatment reduces peroxides but not the 4,6-epoxides. See Smith et al. (1982) in "Lipid Peroxides in Biology and Medicine" (K. Yogi, ed), (Academic Press, New York, pp. 84–105. From these experiments and the reported composition of auto-oxidize cholesterol (Smith, 1981, cited above, pp. 35–62), it may be concluded that the active component of the mixture is one or more of the cholesterol hydroperoxides. Cholesterol-5α,6α-epoxide, 4-cholesten-3-one, 5-cholesten-3β-ol-7-one, and testosterone at 122 µM were without effect in the phosphodiesterase assay.

We claim:

1. The method of suppressing atherogenesis in a human patient, comprising administering to the patient an amount of a cholesterol hydroperoxide effective for reducing aortal deposit of cholesterol, said amount administered being in the dosage range from 0.5 to 25 milligrams of cholesterol hydroperoxide per kilogram of body weight per 24 hours.

2. The method of claim 1 in which the cholesterol hydroperoxide is administered orally.

3. The method of claims 1 and 2 in which the cholesterol hydroperoxide is selected from the group consisting of 3β-hydroxycholest-5-ene-7α-hydroperoxide, 3β-hydroxycholest-5-ene-7β-hydroperoxide, and 3β-hydroxycholest-5-ene-25-hydroperoxide.

4. The method of claims 1 and 2 in which the cholesterol hydroperoxide is 3β-hydroxycholest-5-ene-7α-hydroperoxide.

5. The method of claims 1 and 2 in which the cholesterol hydroperoxide is 3β-hydroxycholest-5-ene-7β-hydroperoxide.

6. The method of claims 1 and 2 in which the cholesterol hydroperoxide is 3β-hydroxycholest-5-ene-25-hydroperoxide.

7. The method of claims 1 or 2 in which the cholesterol hydroperoxide administered has a hydroperoxide group in the 20-position.

8. A medication for prevention and/or treatment of atherogenesis in human patients, comprising an oral dose form of a cholesterol hydroperoxide, said dose form being selected from tablets and capsules.

9. The medication of claim 8 in which said cholesterol hydroperoxide is in admixture with a solid carrier.

10. The medication of claim 8 in which said dose form is a tablet, and said cholesterol hydroperoxide is admixed with a pharmaceutical tableting composition.

11. The medication of claim 8 in which said dose form is a capsule, and said cholesterol hydroperoxide is admixed with a pharmaceutical diluent composition.

12. The medication of claims 8, 9, 10 and 11 in which cholesterol hydroperoxide is selected from the group consisting of 3β-hydroxycholest-5-ene-7α-hydroperoxide, 3β-hydroxycholest-5-ene-7β-hydroperoxide, and 3β-hydroxycholest-5-ene-25-hydroperoxide.

13. The medical use of cholesterol hydroperoxide in which one or more cholesterol hydroperoxides are administered to human patients for control of cholesterol-induced atherogenesis, said cholesterol hydroperoxide being administered in a dosage range from 0.5 to 25 milligrams per kilogram of body weight per 24 hours.

14. The medical use of cholesterol hydroperoxides in which one or more cholesterol hydroperoxides having a hydroperoxide group in the 20-position are administered to human patients for control of cholesterol-induced atherogenesis, said cholesterol 20-hydroperoxide being administered in a dosage range from 0.5 to 25 milligrams per kilogram of body weight per 24 hours.

* * * * *